US00RE43008E

(19) United States
(12) Reissued Patent
Talaber et al.

(10) Patent Number: US RE43,008 E
(45) Date of Reissued Patent: Dec. 6, 2011

(54) ORTHOPEDIC IMPLANT ASSEMBLY

(75) Inventors: David J. Talaber, Livermore, CA (US); James R. Lloyd, Elm Grove, WI (US)

(73) Assignee: Acantha, Inc.

(21) Appl. No.: 10/620,154

(22) Filed: Jul. 15, 2003

Related U.S. Patent Documents

Reissue of:
(64) Patent No.: 6,261,291
Issued: Jul. 17, 2001
Appl. No.: 09/349,519
Filed: Jul. 8, 1999

(51) Int. Cl.
*A61B 17/80* (2006.01)

(52) U.S. Cl. ..... 606/71; 606/289

(58) Field of Classification Search ..... 606/69–73, 606/60, 66, 68
See application file for complete search history.

(56) References Cited

U.S. PATENT DOCUMENTS

| | | | | |
|---|---|---|---|---|
| 591,798 | A | 10/1897 | Strauss | |
| 2,017,247 | A | 10/1935 | Hodge | |
| 2,376,089 | A | 5/1945 | Savageau | |
| 2,782,827 | A | 2/1957 | Rosan | |
| 3,062,253 | A | 11/1962 | Millheiser | |
| 3,350,103 | A | 10/1967 | Ahlstone | |
| 3,561,075 | A | 2/1971 | Selinko | |
| 3,863,959 | A | 2/1975 | Blaschke | |
| 3,896,867 | A | 7/1975 | Gill et al. | |
| 4,017,946 | A | 4/1977 | Soja | |
| 4,074,501 | A | 2/1978 | Sandqvist | |
| 4,280,742 | A | 7/1981 | Justman | |
| 4,288,902 | A | 9/1981 | Franz | |
| 4,380,413 | A | 4/1983 | Dewey | |
| 4,488,543 | A | 12/1984 | Tornier | |
| 4,640,524 | A | 2/1987 | Sedlmair | |
| 4,662,461 | A | 5/1987 | Garrett | |
| 4,696,290 | A | 9/1987 | Steffee | |
| 4,712,959 | A | 12/1987 | Hasan | |
| 4,757,661 | A | 7/1988 | Hasan | |
| 5,054,347 | A | 10/1991 | Johnson et al. | |
| 5,118,235 | A * | 6/1992 | Dill | 411/368 |
| 5,169,597 | A | 12/1992 | Davidson et al. | |
| 5,275,601 | A | 1/1994 | Gogolewski et al. | |
| 5,364,399 | A | 11/1994 | Lowery et al. | |
| 5,372,660 | A | 12/1994 | Davidson et al. | |

(Continued)

FOREIGN PATENT DOCUMENTS

| | | | |
|---|---|---|---|
| DE | 4409833 | A1 | 10/1995 |

(Continued)

*Primary Examiner* — Anu Ramana
(74) *Attorney, Agent, or Firm* — Edward J. Lynch

(57) ABSTRACT

An orthopedic implant assembly comprising a stabilizing element, a securing element which attaches the stabilizing element to the bone, and a stopping member in the stabilizing element which inhibits the securing element from loosening or backing out of the bone. The stabilizing element has at least one bore with the stopping member therein. In one embodiment, the stopping member has a reversibly expandable inner and outer diameter to allow the securing element to pass posteriorly through the stopping member, but thereafter prevent or inhibit the securing element from anteriorly backing out of the posterior section of the transverse passageway. In another embodiment, the stopping member is secured to an anterior section of the transverse passageway, and the head of the securing element generally has a compressed configuration with a diameter less than the diameter of the stopping member, in which configuration the head can pass through the stopping member, and an uncompressed configuration with a diameter larger than the diameter of the stopping member.

105 Claims, 7 Drawing Sheets

U.S. PATENT DOCUMENTS 5,423,826 A 6/1995 Coates et al.
5,509,933 A 4/1996 Davidson et al.
5,520,690 A 5/1996 Errico et al.
5,531,554 A * 7/1996 Jeanson et al. ..... 411/399
5,534,032 A 7/1996 Hodorek
5,549,612 A 8/1996 Yapp et al.
5,569,251 A 10/1996 Baker et al.
5,578,034 A 11/1996 Estes
5,601,552 A 2/1997 Trebing et al.
5,601,553 A 2/1997 Trebing et al.
5,607,426 A 3/1997 Ralph et al.
5,643,265 A 7/1997 Errico et al.
5,725,588 A 3/1998 Errico et al.
5,735,853 A 4/1998 Olerud
5,785,711 A 7/1998 Errico et al.
5,807,396 A 9/1998 Ravch
5,810,819 A 9/1998 Errico et al.
5,843,082 A 12/1998 Yuan et al.
5,876,402 A 3/1999 Errico et al.
5,879,389 A 3/1999 Koshino
5,904,683 A 5/1999 Pohndorf
5,928,243 A 7/1999 Guyer
5,931,838 A 8/1999 Vito
5,935,133 A 8/1999 Wagner et al.
5,961,518 A 10/1999 Errico et al.
5,964,769 A 10/1999 Wagner et al.
5,989,250 A 11/1999 Wagner et al.
5,997,539 A 12/1999 Errico et al.
6,010,503 A * 1/2000 Richelsoph et al. ..... 606/61
6,017,344 A 1/2000 Errico et al.
6,017,345 A * 1/2000 Richelsoph ..... 606/70
6,030,389 A 2/2000 Wagner et al.
6,045,579 A 4/2000 Hochshuler et al.
6,053,921 A 4/2000 Wagner et al.
6,117,173 A 9/2000 Taddia et al.
6,139,550 A * 10/2000 Michelson ..... 606/69
6,193,721 B1 2/2001 Michelson
6,258,089 B1 7/2001 Campbell et al.
6,398,783 B1 6/2002 Michelson
6,620,163 B1 9/2003 Michelson
2006/0122602 A1 6/2006 Konieczynski et al.
2006/0122603 A1 6/2006 Kolb
2006/0122604 A1 6/2006 Gorhan et al.

FOREIGN PATENT DOCUMENTS

DE 19545612 A1 6/1997
WO WO 98/17188 4/1998
WO WO 98/48739 11/1998
WO WO 98/487739 11/1998
WO WO 99/00904 3/1999
WO WO 99/09904 3/1999
WO WO 00/78238 12/2000
WO WO 2006/055156 5/2006

* cited by examiner

ORTHOPEDIC IMPLANT ASSEMBLY

Matter enclosed in heavy brackets [ ] appears in the original patent but forms no part of this reissue specification; matter printed in italics indicates the additions made by reissue.

BACKGROUND OF THE INVENTION

This invention generally relates to the field of medical devices, and particularly to an orthopedic implant for joining bone segments and methods of use thereof.

A variety of medical conditions may necessitate the joining of bone segments together, as for example, in the treatment of broken bones, spinal disorders, or the fusion of vertebrae following the removal of a spinal disk. Orthopedic implants used to join bone segments include rods, plates, and screws. In the case of rods and plates, the implants have been attached to the bone using a variety of methods including cementing and screwing the implant to the bone. The bone is typically drilled out to receive the screw therein, or to receive an anchor having a hollow shank which fixedly receives the screw therein. However, one disadvantage has been the tendency of the implants to loosen or detach from the bone over time.

It would be a significant advance to provide an orthopedic implant for joining bone segments together which durably and securely attaches to the bone.

SUMMARY OF THE INVENTION

This invention is directed to an orthopedic implant assembly generally comprising a stabilizing element, a securing element which attaches the stabilizing element to the patient's bone, and a stopping member in the stabilizing element which defines at least in part a passageway and which inhibits or prevents the securing element from loosening or backing out of the bone.

The stabilizing element is generally a plate or rod, which has at least one bore therein having a first opening in the anterior surface of the stabilizing element, a second opening in the posterior surface of the stabilizing element, and a transverse passageway extending from the first opening to the second opening. The term posterior should be understood to mean an inner portion of the assembly closer to the bone to which the assembly is attached, and the term anterior should be understood to mean an outer portion of the assembly farther away from the bone.

In one embodiment, the stopping member defines a reversibly expandable passageway, and is biased to the unexpanded, or smaller diameter, passageway configuration. In one embodiment, the biased stopping member comprises an annular collar having a reversibly expandable inner diameter. The biased stopping member may be configured to be positioned in a groove in the transverse passageway after the securing element is in place in the transverse passageway of the stabilizing element. Alternatively, in a presently preferred embodiment, the biased stopping member is configured to allow the securing element to pass posteriorly through the stopping member passageway from the anterior surface of the stabilizing element into a posterior section of the transverse passageway. In another embodiment, the biased stopping member is secured to the stabilizing element within the transverse passageway, and is deflectable. The deflectable stopping member reversibly flexes as the head of the securing element is posteriorly displaced through the deflectable stopping member to expand the passageway defined by the stopping member. The deflectable stopping member is biased to the undeflected or smaller diameter passageway configuration. The stopping member prevents the securing element from anteriorly backing out of the posterior section of the transverse passageway. As a result, the securing element durably attaches the stabilizing element to the bone.

The securing element is configured to attach to bone, and generally comprises an elongated body and a head at one end of the body and integral therewith. The term integral should be understood to mean the securing element is a one-piece unit, with the head secured to the body so that there is no relative movement between the head and the body. In one embodiment, the securing element is selected from the group consisting of screws, pins, and nails. In a presently preferred embodiment where the collar is seated within the groove in the stabilizing element before the securing element is advanced therein, the head of the securing element has a shaped posterior surface which contacts the collar and gradually expands the collar as the head is displaced into the posterior section of the transverse passageway of the stabilizing element. In a presently preferred embodiment, the head of the securing element has a curved posterior surface. However, other suitable shapes may be used including tapered posterior surfaces.

The invention also includes methods of attaching an orthopedic implant assembly to a bone of a patient. The bone is typically prepared for receiving the body of the securing element, as for example by drilling a cavity into the bone, and/or tapping the cavity. A method generally comprises positioning the posterior surface of the stabilizing element against the surface of the bone, with the stopping member within the groove of the stabilizing element in the unexpanded configuration, introducing the body of the securing element into the transverse passageway, posteriorly displacing the head of the securing element through the stopping member and thereby expanding the stopping member, and attaching the stabilizing element to the bone by advancing the head of the securing element posteriorly of the stopping member so that the stopping member contracts and returns to a smaller transverse, i.e., unexpanded diameter, configuration. The head of the securing element is positioned within a posterior section of the transverse passageway between the stopping member and the second opening in the stabilizing element, and the body of the securing element is positioned within the patient's bone. In an alternative embodiment, the stopping member may be placed within the groove after the head of the securing element is positioned within the posterior section of the transverse passageway. The stabilizing element is attached to the bone by the securing element, which is attached to the bone and retained within the transverse passageway.

In another embodiment of the invention, the head of the securing element can be reversibly compressed, and the stopping member is secured to an anterior section of the transverse passageway. The stopping member defines a passageway with a fixed diameter, but the compressed configuration of the head of the securing element has a diameter less than the diameter of the stopping member so that the head can pass through the stopping member passageway. In the uncompressed configuration, the head of the securing element has a diameter larger than the diameter of the stopping member and the diameter of the second opening in the stabilizing element, so that the head can be advanced posteriorly of the stopping member and retained within the transverse passageway between the stopping member and the second opening.

To facilitate the correct placement of the orthopedic implant assembly on the bone, the transverse passageway between the collar and the second opening in the stabilizing element may be configured so that the securing element may be angularly displaceable therein and the body of the securing element may be positioned at an angle within the patient's bone.

In the assembly of the invention, the securing element is prevented from backing out of the bone by the interaction of the securing element head and the stopping member. As a result, a separate anchor means implanted in the bone to receive the screw is not required, and the resulting loss of bone and intraoperative time required to implant the anchor is avoided. Moreover, in a preferred embodiment, the stopping member is within the transverse passageway at the beginning of the procedure, so that the surgeon can attach the implant assembly to the bone with the single motion of advancing the securing element through the stopping member passageway and into the bone. The implant assembly of the invention thus reduces the time required to attach the assembly to the bone and provides improved implant performance.

The orthopedic implant assembly of the invention can be durably attached to bone, and the securing element prevented from significantly backing out of the bone due to the head of the securing element being retained within the stabilizing element. These and other advantages of the invention will become more apparent from the following detailed description of the invention and the accompanying exemplary drawings.

DETAILED DESCRIPTION OF THE INVENTION

Figure 1:
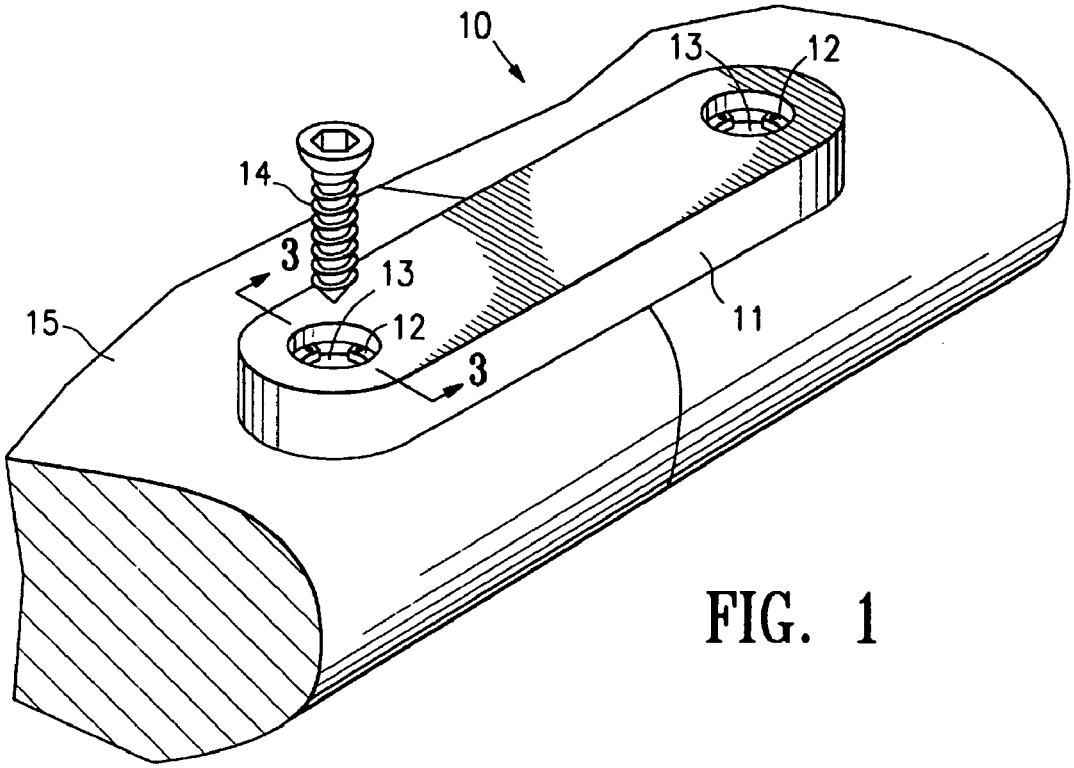
FIG. 1 is an elevational view of an orthopedic implant assembly which embodies features of the invention.

FIG. 1 illustrates one embodiment of the orthopedic implant assembly 10 of the invention, generally including a stabilizing element 11, with a biased stopping member 12 in a bore 13 therein, and a securing element 14, configured for securing to a patient's bone 15. In the embodiment illustrated in FIG. 1, the biased stopping member comprises an annular collar, although a variety of suitable members may be used, as for example, one or more contractible fingers biased to extend into the transverse passageway (not shown).

Figure 2:
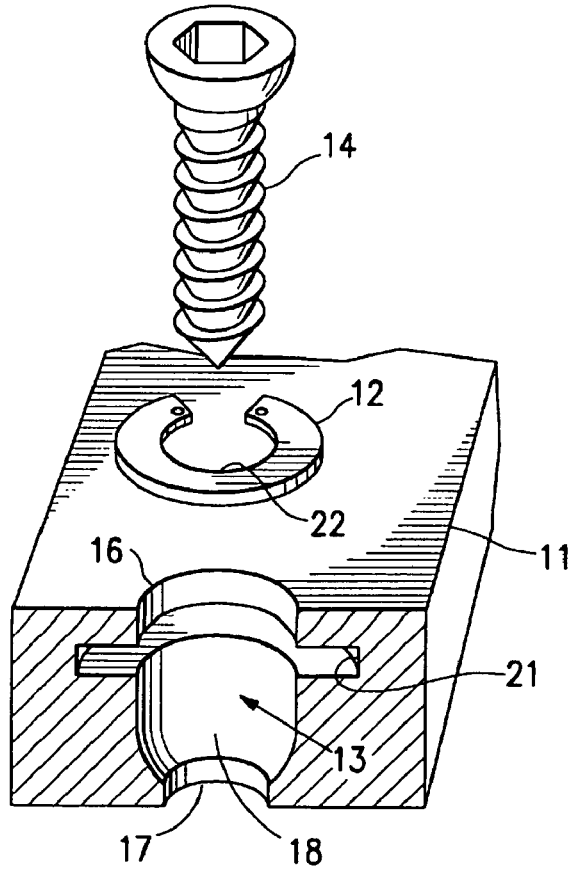
FIG. 2 is an exploded view, partially in section, of the orthopedic implant assembly shown in FIG. 1.
Figure 3:
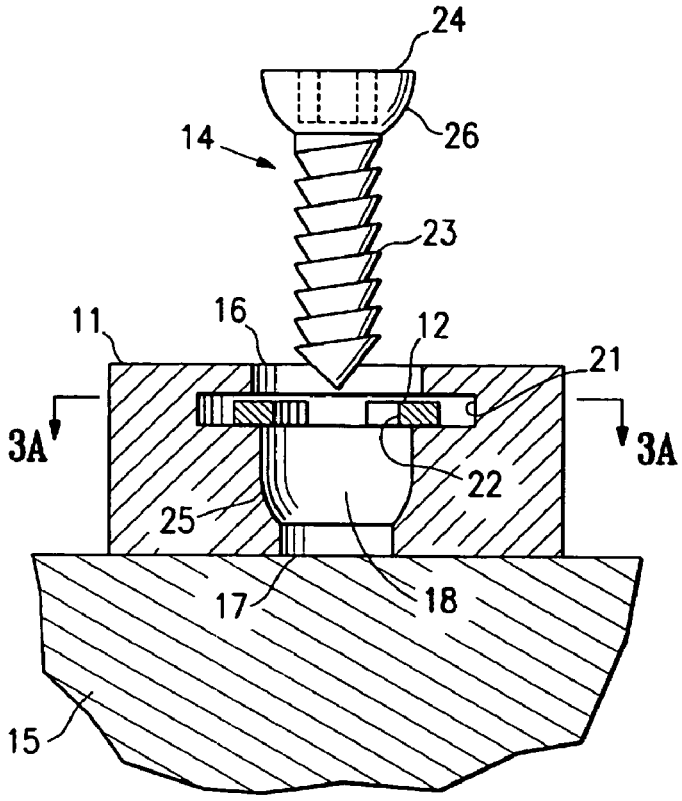
FIG. 3 is a cross section of the orthopedic implant assembly shown in FIG. 1 taken along lines 3-3.
Figure 3A:
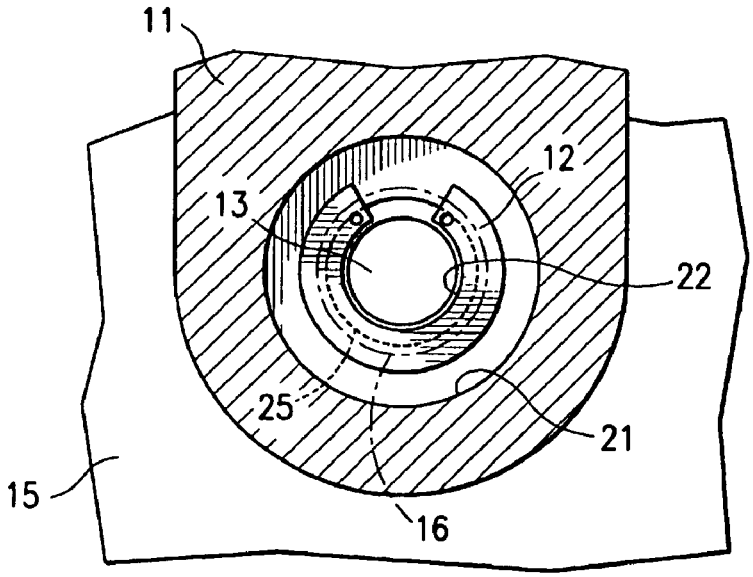
FIG. 3A is a transverse cross section of the orthopedic implant assembly shown in FIG. 3 taken along lines 3A-3A.

As best illustrated in FIG. 2 showing an exploded, partially in section, view of the assembly shown in FIG. 1, the bore 13 of the stabilizing element has a first opening 16 in an anterior surface of the stabilizing element, a second opening 17 in a posterior surface of the stabilizing element, a transverse passageway 18 extending therein, and a groove 21 in an anterior portion of the transverse passageway. Annular collar 12 defines a passageway 22, and is configured to be seated within the groove 21, and has a reversibly expandable inner and outer diameter. As illustrated in FIG. 3, illustrating the assembly shown in FIG. 1 partially in section taken along lines 3-3, and FIG. 3A illustrating a transverse cross sectional view of the assembly shown in FIG. 3 taken along lines 3A-3A, the annular collar 12 is biased to an unexpanded outer diameter which is less than the diameter of the groove and greater than the diameter of the transverse passageway, so that the collar seats within the groove. The expanded outer diameter of the collar is less than the diameter of the groove, and the height of the collar is less than the height of the groove, so that the collar can be expanded therein.

The securing element 14 has an elongated body 23 and an integral head 24 secured to one end of the body 23. In a presently preferred embodiment of the invention illustrated in FIG. 1, the securing element comprises a screw. The head of the securing element is configured to be posteriorly displaceable through the passageway 22 of the collar seated within the groove, from an anterior to a posterior surface of the collar, and retained within a posterior section 25 of the transverse passageway 18 between the posterior surface of the collar 12 and the second, i.e., posterior, opening 17 in the stabilizing element. In the embodiment illustrated in FIG. 1, the head of the securing element has a curved posterior surface 26 with a convex shape and with a smaller diameter than an anterior surface of the head. The curved posterior surface 26 has a minimum outer diameter which is smaller than the unexpanded inner diameter of the collar, and which is positionable within the passageway of the collar, to contact and expand the collar as the head is displaced posteriorly therein.

Figure 4:
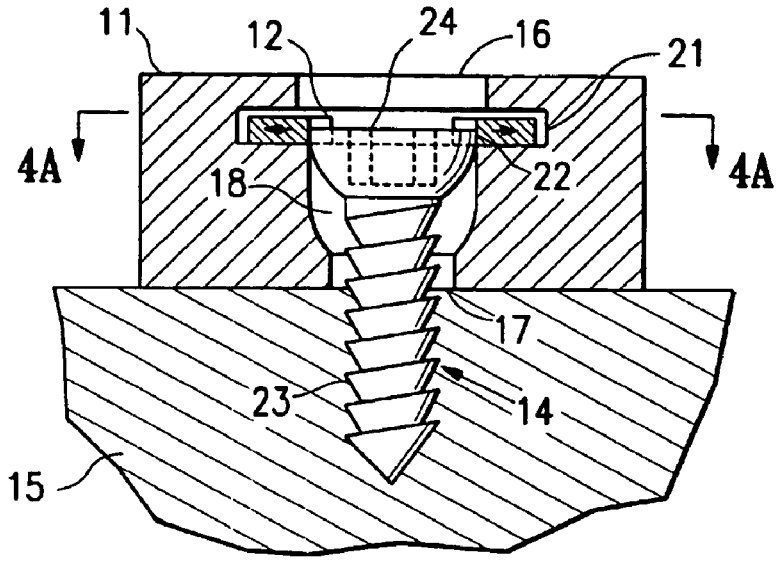
FIG. 4 illustrates the orthopedic implant assembly shown in FIG. 3, as the securing element is being advanced into the patient's bone.
Figure 4A:
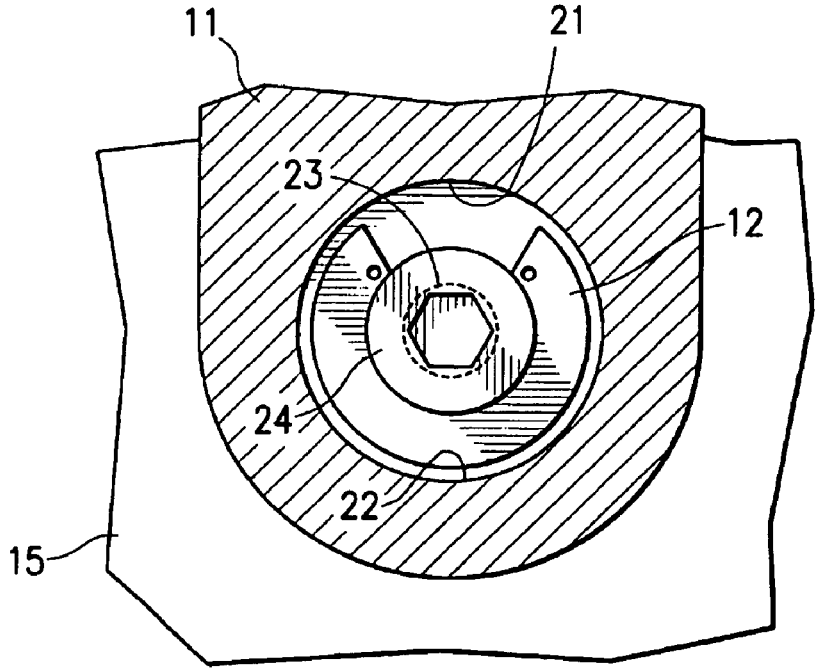
FIG. 4A is a transverse cross section of the assembly shown in FIG. 4, taken along lines 4A-4A.
Figure 5:
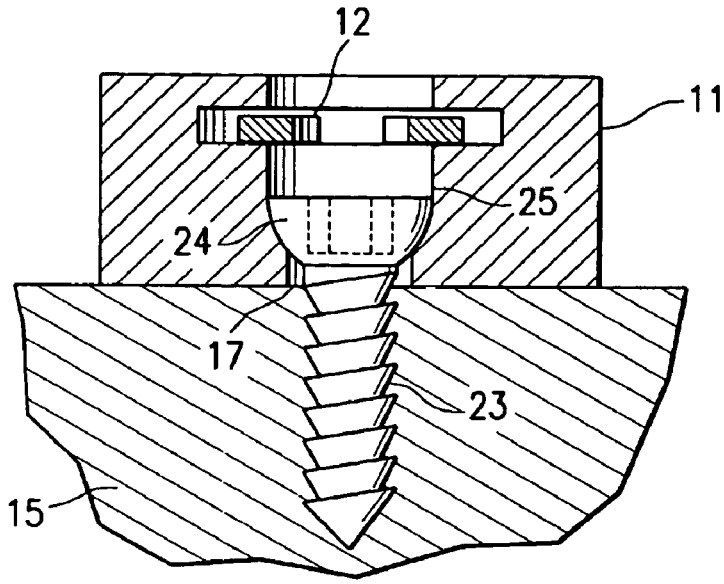
FIG. 5 illustrates the orthopedic implant assembly shown in FIG. 3, with the securing element advanced into the posterior section of the transverse passageway of the stabilizing element.

FIGS. 3-5 illustrate the attachment of the assembly to the patient's bone. As illustrated in FIG. 3, the stabilizing element is positioned against a surface of a bone 15, and the posterior end of the body of the securing element 14 is placed within the stabilizing element transverse passageway. The head 24 of the securing element is posteriorly advanced within the passageway 22 of the collar 12, thereby applying a radially expanding force against an inner surface of the collar to expand the inner diameter of the collar, as illustrated in FIG. 4 showing the expanded collar and the head of the securing element partially displaced through the collar passageway. Arrows in FIG. 4 illustrate the expansion of the collar as the head of the securing element is passed therethrough. FIG. 4A illustrates a transverse cross section of the assembly shown in FIG. 4, taken along lines 4A-4A. The expanded inner diameter of the collar is therefore larger than the maximum diameter of the head of the securing element, to allow the head of the securing element to pass posteriorly through the collar. The head of the securing element is advanced posteriorly of the collar and into the posterior section 25 of the transverse passageway, so that the collar returns to the unexpanded configuration having an unexpanded inner diameter smaller than the maximum diameter of the head of the securing element, as illustrated in FIG. 5. In the embodiment illustrated in FIG. 5, the flat anterior surface of the head of the securing element has a diameter which is larger than the unexpanded inner diameter of the collar, and the posterior surface of the collar is perpendicular to the longitudinal axis of the transverse passageway. Thus, the anterior surface of the head will butt up against the posterior surface of the collar without expanding the collar, to prevent the securing element from being anteriorly displaced out of the posterior section of the transverse passageway. In the embodiment illustrated in the FIG. 5, a posterior portion of the transverse passageway is curved to conform to the curved posterior surface of the head, providing maximum contact between the securing element and the stabilizing element. The curved surfaces of the posterior portion of the transverse passageway and the posterior surface of the head have the same radius of curvature, and the diameter of the curved surface of the head is large enough so that the wall defining the transverse passageway contacts the head around the circumference of the curved posterior surface of the head, but is small enough so that the head can be displaced within the transverse passageway. With the head of the securing element positioned within the posterior section 25 of the transverse passageway, the body of the securing element is embedded in, and secured to, the bone of the patient.

Figure 6:
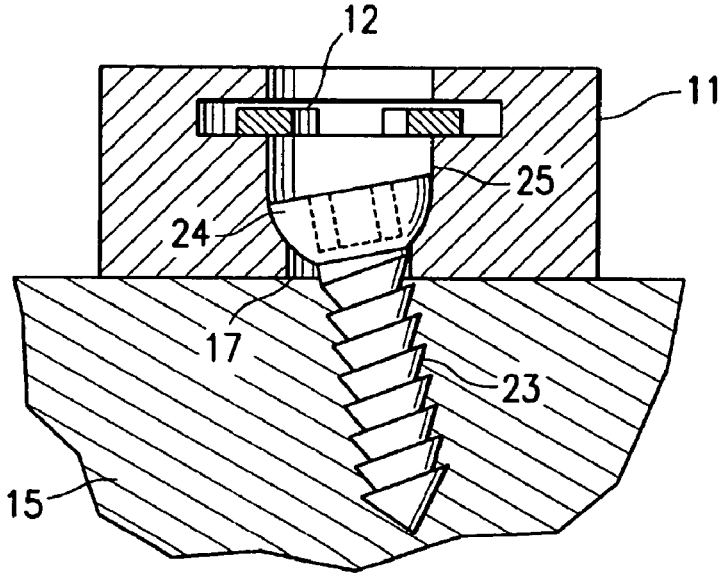
FIG. 6 illustrates the orthopedic implant assembly shown in FIG. 3, with the securing element angularly disposed within the patient's bone.
Figure 7:
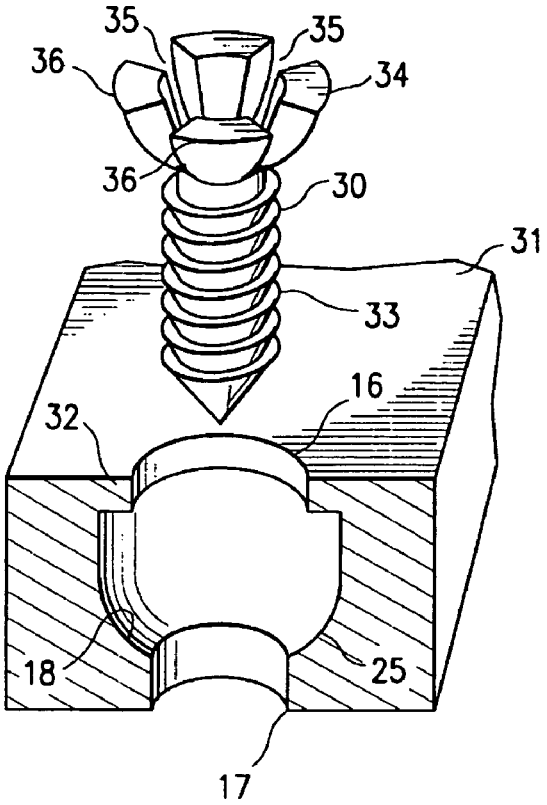
FIG. 7 is an exploded view, partially in section, of an orthopedic implant assembly having a securing element with a compressible head, which embodies features of the invention.

In the embodiment illustrated in FIG. 5, the posterior section 25 of the transverse passageway is sufficiently longer than the head 24 of the securing element so that the head can be displaced anteriorly and posteriorly, and is thus longitudinally displaceable within the posterior section of the transverse passageway. Additionally, the body of the securing element 23 has a smaller diameter than the diameter of the second opening 17 in the stabilizing element, and can be displaced from side to side, i.e., medial-lateral displacement, within the second opening 17. As a result, the securing element is angularly displaceable within the transverse passageway posterior section 25 between the collar 12 and the second opening 17 in the stabilizing element, as illustrated in FIG. 6. The securing element can thus be tilted within the transverse passageway at an angle relative to the transverse passageway longitudinal axis, to facilitate positioning the securing element at a desired location in the bone by advancing the body of the securing element within the bone at an angle relative to the surface of the bone. The securing element can be angularly displaced up to an angle of about 45°, preferably up to about 20° relative the longitudinal axis of the transverse passageway.

The stopping member 12 is preferably elastically deformable, and formed of titanium, and superelastic or pseudoelastic materials such as NiTi alloys. The unexpanded inner diameter of the stopping member is about 0.1 to about 40 mm, preferably about 0.5 to about 20 mm, and is about 0.05 to about 20 mm, preferably about 0.1 to about 15 mm less than the maximum transverse dimension of the head of the securing element. The unexpanded outer diameter of the stopping member is about 0.2 to about 50 mm, preferably about 1.0 to about 30 mm. The expanded inner diameter of the stopping member is about 0.15 to about 50 mm, preferably about 0.75 to about 30 mm, and the expanded outer diameter of the stopping member is about 0.5 to about 60 mm, preferably about 1.5 to about 40 mm. The height of the stopping member is about 0.01 to about 5 mm, preferably about 0.05 to about 3 mm.

Figure 9:
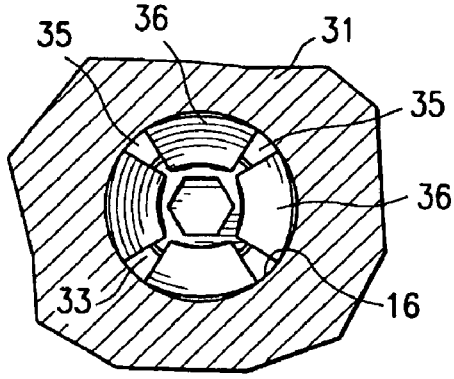
FIGS. 9 is a transverse cross section of the assembly shown in FIG. 8, taken along lines 9-9.
Figure 8:
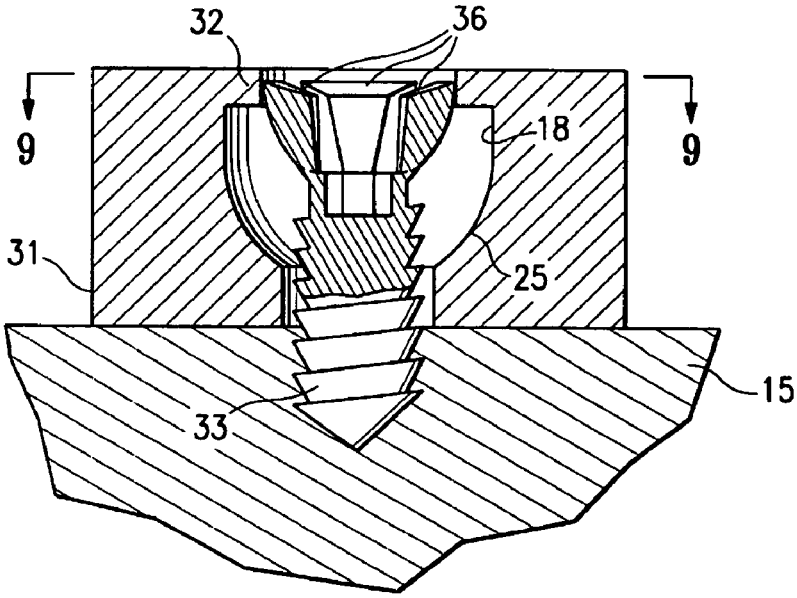
FIG. 8 illustrates the orthopedic implant assembly shown in FIG. 7 as the securing element is being advanced into the patient's bone.
Figure 10:
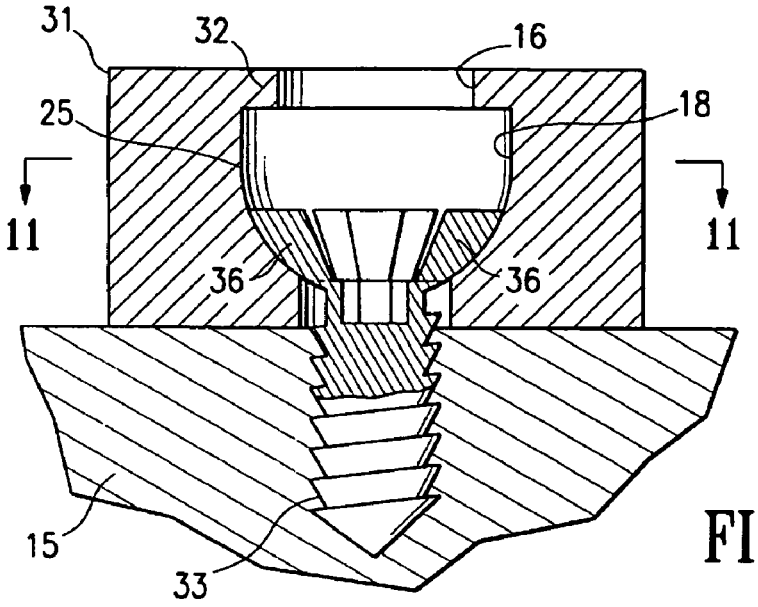
FIG. 10 illustrates the orthopedic implant assembly shown in FIG. 7 with the securing element advanced into the posterior section of the transverse passageway of the stabilizing element.
Figure 11:
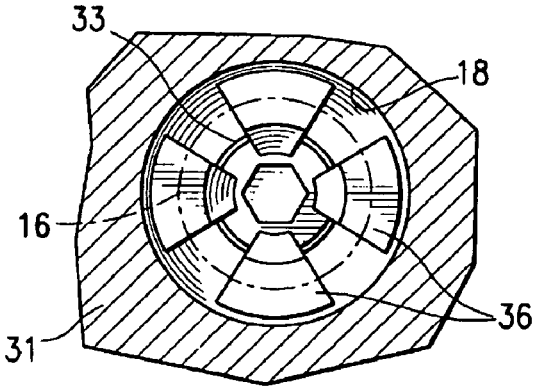
FIG. 11 is a transverse cross section of the assembly shown in FIG. 10, taken along lines 11-11.
Figure 12:
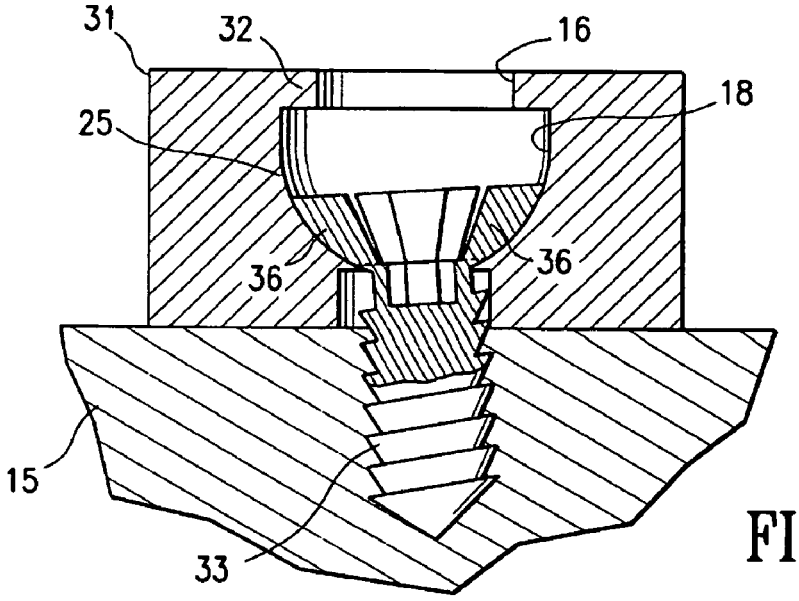
FIG. 12 illustrates the orthopedic implant assembly shown in FIG. 7, with the securing element angularly disposed within the patient's bone.

FIGS. 7-12 illustrate another embodiment of the invention, generally comprising a securing element 30, and a stabilizing element 31 similar to the stabilizing element in the embodiment illustrated in FIG. 1, except the stopping member is not seated within a groove in the transverse passageway 18. Instead, a stopping member 32 is provided at an anterior section of the transverse passageway, which may be formed integrally with the stabilizing element or as a separate member secured thereto. In the embodiment illustrated in FIG. 7, the stopping member is a collar at the anterior end of the transverse passageway and defining the first opening 16 in the stabilizing element 31. The securing element 30 has an elongated body 33, and head 34 secured to one end of the body having a compressed configuration and an uncompressed configuration. In the embodiment illustrated in FIG. 7, the head has a plurality of slots 35 defining circumferentially spaced members 36 having posterior ends secured to the body of the securing element. The circumferentially spaced members 36 have anterior ends radially moveable toward a longitudinal axis of the head to form the compressed configuration, having a diameter less than the inner diameter of the collar. FIG. 8 illustrates the head of the securing element in the compressed configuration within the passageway defined by the collar. FIG. 9 illustrates a transverse cross sectional view of the assembly shown in FIG. 8, taken along lines 9-9. FIG. 10 illustrates the head of the securing element advanced posteriorly of the collar and into the posterior section of the transverse passageway, thereby returning the circumferentially spaced members 36 to the uncompressed configuration by release of the radially compressive force of the collar. FIG. 11 illustrates a transverse cross section of the assembly shown in FIG. 10, taken along lines 11-11, with the first opening 16 shown in phantom. The securing element is angularly and longitudinally displaceable within the transverse passageway posterior section 25, as discussed above with regard to the embodiment illustrated in FIG. 1, and as illustrated in FIG. 12.

Figure 13:
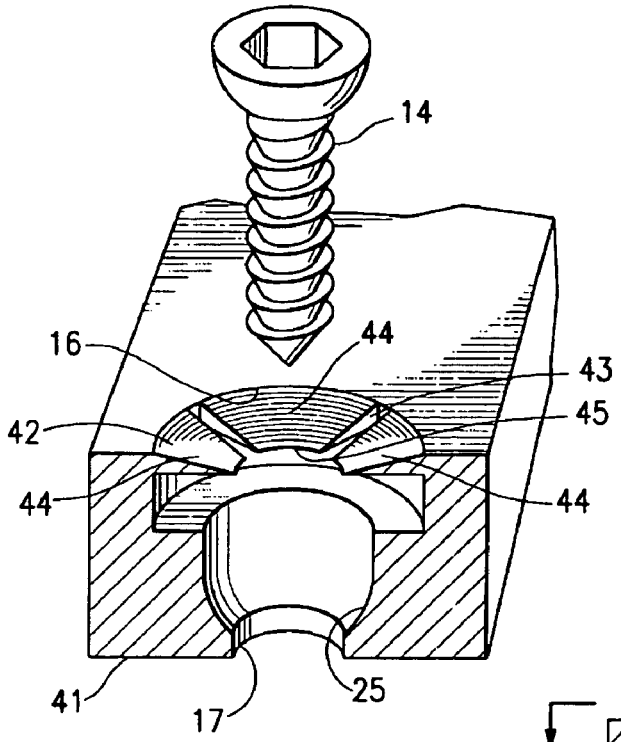
FIG. 13 is an exploded view, partially in section, of an orthopedic implant assembly having a deflectable stopping member, which embodies features of the invention.
Figure 14:
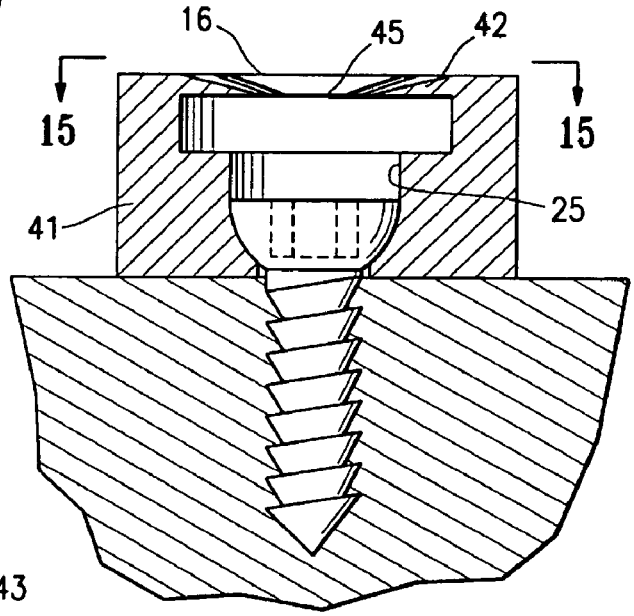
FIG. 14 illustrates the orthopedic implant assembly shown in FIG. 13 with the securing element advanced into the posterior section of the transverse passageway of the stabilizing element.
Figure 15:
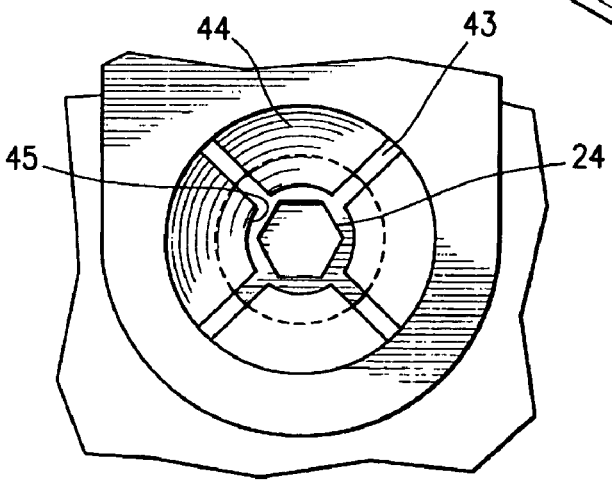
FIGS. 15 is a plan view of the assembly shown in FIG. 14, taken along lines 15-15.

FIGS. 13-15 illustrate another embodiment of the invention, generally comprising a stabilizing element 41 similar to the stabilizing element in the embodiment illustrated in FIG. 1, except with a deflectable stopping member 42 provided in an anterior section of the transverse passageway, which may be formed integrally with the stabilizing element or as a separate member secured thereto. In the embodiment illustrated in FIG. 13, the stopping member comprises a collar 42 having a plurality of slots 43 defining circumferentially spaced members 44 and a tapered or sloping anterior surface providing axial flexibility in a posterior direction, so that the collar deflects posteriorly when the head of the securing element is posteriorly displaced through the collar. As a result, the circumferentially spaced members 44 have a wedge shape and a height which tapers towards the central passageway 45 defined by the collar, which facilitates displacing the head of the securing element therethrough and reversibly enlarging the passageway 45. In the embodiment illustrated in FIG. 13, the collar is integrally formed with the stabilizing element 41 at the anterior end of the transverse passageway, and defines the first opening 16 in the stabilizing element 41. The securing element may be the same as, or similar to, the securing element 14 discussed above in connection with the embodiment illustrated in FIG. 1, and as illustrated in FIG. 13. However, securing element 30 having head 34 with a compressed configuration and an uncompressed configuration, as discussed above in connection with the embodiment illustrated in FIG. 7, may also be used. FIG. 15 illustrates a plan view of the assembly shown in FIG. 14, taken along lines 15-15, with the head of the securing element 14 partially in phantom. The angular and longitudinal displacement of the securing member in the posterior section 25 of the transverse passageway is as discussed above.

The stabilizing element is preferably formed of a metal such as titanium or stainless steel. The length of the stabilizing element is typically about 7 to about 300 mm, preferably about 13 to about 200 mm, and the width of the stabilizing element is typically about 5 to about 50 mm, preferably about 10 to about 30 mm. The height of the stabilizing element is typically about 0.5 to about 10 mm, preferably about 1.0 to about 6.0 mm although the dimensions of the stabilizing element will vary depending on the application for which the assembly is to be used.

The securing element is preferably formed of a metal, such as titanium or stainless steel. The head of the securing element is configured, as for example with a hexagonal opening, for releasable connection to a tool for advancing the securing element into the bone. The body of the securing element has a length of about 2 to about 50 mm, preferably about 5 to about 20 mm, and the head of the securing element has a length of about 0.05 to about 1.5 mm, preferably about 0.5 to about 1.0 mm. One skilled in the art will recognize that a variety of suitable securing elements may be used, which may be optimized for use in a particular orthopedic environment, as is well known in the art. For example, a high thread pitch may be used to limit screw back out from bone.

The assembly of the invention is suitable for use in a variety of medical procedures, including securing fractured bone segments or vertebrae following disk removal. In the illustrated embodiments, the stabilizing element comprises a plate, although other suitable elements such as rods may be used. Additionally, the stabilizing element may be shaped to conform to the surface of the bone or bones to which it will be attached. For example, a presently preferred embodiment of the stabilizing element comprises a plate with a concave posterior surface, and is configured for attaching to vertebrae.

While the present invention has been described herein in terms of certain preferred embodiments, those skilled in the art will recognize that modifications and improvements may be made without departing from the scope of the invention. For example, while the stopping member is discussed primarily in terms of a collar, other configurations may also be used. Additionally, while a particular feature may be discussed in connection with one embodiment, it should be understood that features of one embodiment may be used with the other embodiments herein.

What is claimed is:

1. An orthopedic implant assembly, comprising a) a stabilizing element having an anterior surface, a posterior surface, and at least one bore, the bore having a first opening in the anterior surface, a second opening in the posterior surface smaller than the first opening, and a transverse passageway extending from the first opening to the second opening;

b) a biased stopping member defining at least in part a reversibly expandable passageway having a smaller diameter configuration and a larger diameter configuration; and c) a securing element having an elongated body, and a head at one end of the body and integral therewith, the head having a maximum diameter greater than the smaller diameter configuration of the passageway defined by the biased stopping member and greater than the second opening in the stabilizing element, so that the head is retained within the transverse passageway between the biased stopping member and the second opening in the stabilizing element.

2. The assembly of claim 1 wherein the biased stopping member comprises a collar defining a passageway, enlargeable from an unexpanded inner diameter to an expanded inner diameter, wherein the head of the securing element has a maximum diameter greater than the unexpanded inner diameter of the collar and less than the expanded inner diameter of the collar.

3. The assembly of claim 2 wherein the head of the securing element has a curved posterior surface which has a minimum outer diameter smaller than the unexpanded inner diameter of the collar, configured to be displaceable posteriorly of the collar through the passageway of the collar from an anterior to a posterior surface thereof.

4. The assembly of claim 2 wherein the bore has a groove in an anterior portion of the transverse passageway having a diameter and a height, and wherein the collar is a reversibly expandable annular collar seated in the groove, the collar having an expanded outer diameter, and an unexpanded outer diameter which is less than the diameter of the groove and greater than a diameter of the transverse passageway.

5. The assembly of claim 4 wherein the head of the securing element has a curved posterior surface which has a minimum outer diameter smaller than the unexpanded inner diameter of the collar, and which is configured to contact the collar anterior surface and expand the collar as the head is displaced posteriorly through the collar passageway.

6. The assembly of claim 2 wherein the collar is secured to an anterior section of the transverse passageway, and has a plurality of slots and circumferentially spaced members, the circumferentially spaced members having a deflected configuration defining the expanded inner diameter of the collar.

7. The assembly of claim 6 wherein the head of the securing element has a curved posterior surface which has a minimum outer diameter smaller than the unexpanded inner diameter of the collar, and which is configured to contact the collar anterior surface and deflect the circumferentially spaced members away from a longitudinal axis of the transverse passageway as the head is displaced posteriorly through the collar passageway.

8. The assembly of claim 6 wherein the collar has an anterior surface which tapers toward a center of the transverse passageway.

9. The assembly of claim 3 wherein a posterior portion of the transverse passageway is curved to conform to the curved posterior surface of the head.

10. The assembly of claim 1 wherein the head of the securing element is longitudinally displaceable within the transverse passageway between a posterior surface of the biased stopping member and the second opening in the posterior surface of the stabilizing element.

11. The assembly of claim 10 wherein the body of the securing element has a diameter smaller than the second opening in the stabilizing element, and the securing element may be angularly displaced within the transverse passageway and the second opening in the stabilizing element.

12. The assembly of claim 1 wherein the stabilizing element includes at least two bores.

13. The assembly of claim 1 wherein the stabilizing element is configured to conform to and extend between at least two bone segments.

14. The assembly of claim 13 wherein the stabilizing element has a curved surface.

15. The assembly of claim 1 wherein the stabilizing element is selected from the group consisting of rods and plates.

16. The assembly of claim 1 wherein the securing element is selected from the group consisting of screws and nails.

17. The assembly of claim 2 wherein the collar is formed of an elastically deformable material.

18. The assembly of claim 2 wherein the collar is formed of a material selected from the group consisting of titanium and superelastic material.

19. The assembly of claim 2 wherein the collar has a posterior surface perpendicular to a longitudinal axis of the transverse passageway.

20. The assembly of claim 4 wherein the collar has a height less than the height of the groove.

21. A method of attaching an orthopedic implant assembly to a bone of a patient, comprising a) positioning a stabilizing element against a surface of the patient's bone, the stabilizing element having an anterior surface, a posterior surface, and at least one bore, the bore having a first opening in the anterior surface, a second opening in the posterior surface smaller than the first opening, and a transverse passageway extending from the first opening to the second opening, and a biased stopping member within the bore and defining at least in part a reversibly expandable passageway having a smaller diameter configuration and a larger diameter configuration;

b) providing a securing element having an elongated body, and a head at one end of the body and integral therewith, the head having a maximum diameter greater than the smaller diameter configuration of the passageway defined by the biased stopping member and greater than the second opening in the stabilizing element, so that the head is retained within the transverse passageway between the biased stopping member and the second opening in the stabilizing element;

c) positioning the body of the securing element in the transverse passageway and posteriorly advancing the head of the securing element within the passageway defined by the biased stopping member and thereby displacing the biased stopping member to form the larger diameter configuration passageway defined thereby; and d) attaching the stabilizing element to the bone by advancing the head of the securing element posteriorly of the biased stopping member so that the passageway defined thereby returns to the smaller diameter configuration, to position the head within a posterior section of the transverse passageway between the biased stopping member and the second opening in the stabilizing element, and to position the body of the securing element within the patient's bone, so that the securing element is attached to the bone and is retained within the posterior section of the transverse passageway of the stabilizing element.

22. The method of claim 21 including, after the head of the securing element is positioned between the biased stopping member and the second opening in the stabilizing element, the step of longitudinally and angularly displacing the head of the securing element within the transverse passageway, so that the body of the securing element is positioned at an angle within the patient's bone relative to the surface of the bone.

23. An orthopedic implant assembly, comprising a) a stabilizing element having an anterior surface, a posterior surface, and at least one bore, the bore having a first opening in the anterior surface, a second opening in the posterior surface smaller than the first opening, and a transverse passageway extending from the first opening to the second opening, and a stopping member at an anterior section of the transverse passageway; and b) a securing element having an elongated body and a head secured to one end of the body, the head having a reversibly compressed configuration with a compressed diameter less than the diameter of the first opening and an uncompressed configuration with a diameter greater than a diameter of the stopping member and the second opening, so that the head of the securing element is retained within the transverse passageway between the stopping member and the second opening in the stabilizing element.

24. The assembly of claim 23 wherein the head of the securing element is configured to be displaceable posteriorly through the stopping member from an anterior to a posterior surface thereof.

25. The assembly of claim 23 wherein the head of the securing element has a plurality of slots and circumferentially disposed members, the circumferentially disposed members having posterior ends secured to the body of the securing element, and anterior ends radially moveable toward a longitudinal axis of the head of the securing element to form the compressed configuration and away from the longitudinal axis to form the uncompressed configuration.

26. The assembly of claim 23 wherein the stopping member is at the anterior end of the transverse passageway and defines the first opening in the stabilizing element.

27. The assembly of claim 23 wherein the stopping member has a posterior surface perpendicular to a longitudinal axis of the transverse passageway.

28. A method of attaching an orthopedic implant assembly to a bone of a patient, comprising a) positioning a stabilizing element against a surface of the patient's bone, the stabilizing element having an anterior surface, a posterior surface, and at least one bore, the bore having a first opening in the anterior surface, a second opening in the posterior surface smaller than the first opening, and a transverse passageway extending from the first opening to the second opening, and a stopping member at an anterior section of the transverse passageway;

b) providing a securing element having an elongated body and a head secured to one end of the body, the head having a reversibly compressed configuration with a compressed diameter less than a diameter of the first opening and an uncompressed configuration with a diameter greater than the diameter of the stopping member and the second opening, so that the head of the securing element is retained within the transverse passageway between the stopping member and the second opening in the stabilizing element;

c) positioning the body of the securing element in the transverse passageway and posteriorly advancing the head of the securing element within a passageway defined by the stopping member and thereby compressing the diameter of the head of the securing element; and d) attaching the stabilizing element to the bone by advancing the head of the securing element posteriorly of the stopping member so that the diameter of the head of the securing element returns to the uncompressed configuration, to position the head within a posterior section of the transverse passageway between the stopping member and the second opening in the stabilizing element and the body of the securing element within the patient's bone, so that the securing element is attached to the bone and is retained within the posterior section of the transverse passageway of the stabilizing element.

*29. The assembly of claim 4 wherein the collar has a height less than the height of the groove.*

*30. The assembly of claim 10 wherein the body of the securing element has a transverse dimension smaller than the second opening of the stabilizing element, and wherein the securing element may be angularly displaced within a posterior portion of the bore of the stabilizing element.*

*31. The assembly of claim 10 wherein the stabilizing element is selected from the group consisting of rods and plates.*

*32. The assembly of claim 10 wherein the securing element is selected from the group consisting of screws and nails.*

*33. The assembly of claim 13 wherein the stabilizing element has a concave posterior surface.*

*34. The assembly of claim 1 wherein the stabilizing element includes at least two bores.*

*35. The assembly of claim 1 wherein the stabilizing element is configured to conform to and extend between at least two bone segments.*

*36. A method of attaching an orthopedic implant assembly to a bone of a patient, comprising*

*a) providing*

*a securing member with an elongated body and an enlarged integral portion having a maximum transverse dimension,*

*an attachment member which has an anterior surface and a posterior surface and which has at least one bore extending through the attachment member from the anterior surface to the posterior surface and is configured to receive the securing member, the bore having an anterior bore portion, and a posterior bore portion with at least one transverse dimension smaller than a transverse dimension of the anterior bore portion and smaller than the maximum transverse dimension of the enlarged integral portion of the securing member, and*

*a stopping member which has a first configuration which allows passage of the enlarged integral portion of the securing member and has a second configuration that reduces a transverse dimension of the bore that is smaller than the maximum transverse dimension of the enlarged integral portion of the securing member in order to retain the enlarged integral portion of the securing member within the posterior bore portion of the attachment member wherein the stopping member has an anterior surface and a posterior surface;*

*b) positioning the attachment member with at least part of the posterior surface thereof against a surface of the patient's bone; and*

*c) attaching the securing member to the patient's bone by advancing the securing member within the bore of the attachment member until the enlarged integral portion of the securing member passes the stopping member thereby displacing the stopping member to the first configuration and is disposed in the posterior bore portion, the stopping member then returning to the second configuration to retain the enlarged integral portion within the posterior bore portion; and wherein the enlarged integral portion of the securing member is retained within the posterior bore portion below the posterior surface of the stopping member.*

*37. The method of claim 36 wherein the securing member is angularly displaceable within the posterior bore portion so that the securing member may be secured within the patient's bone at an angle relative to a longitudinal axis of the bore.*

*38. An orthopedic implant assembly, comprising:*

*a) a securing element with an elongated body and an enlarged head;*

*b) an attachment member comprising*

*an attachment component which has at least one bore configured to receive the securing element, the bore having a first bore portion, and a second bore portion having at least one smaller transverse dimension than transverse dimensions of the first bore portion;*

*a stopping surface which reduces a transverse configuration of the first bore portion to retain the enlarged head of the securing element within the bore of the attachment member between the stopping surface and the second bore portion, and*

*a third bore portion between the stopping surface and the second bore portion having a surface configured to conform at least in part to part of the enlarged head of the securing element received by the bore; and*

*c) the enlarged head of the securing element having a reversibly compressed configuration with transverse dimensions less than the reduced transverse configuration of the first bore portion formed at least in part by the stopping surface and having an uncompressed configuration with a transverse dimension greater than the reduced transverse configuration of the first bore portion and the second bore portion, so that the head of the securing element is retained within the bore between the stopping surface and the second bore portion in the attachment component.*

*39. The implant assembly of claim 38 wherein the head of the securing element is configured to be displaceable posteriorly through the stopping surface from an anterior to a posterior portion thereof.*

*40. The implant assembly of claim 38 wherein the head of the securing element has a plurality of slots and circumferentially disposed members having posterior ends secured to the body of the securing element, and anterior ends radially moveable toward a longitudinal axis of the head of the securing element to form the compressed configuration and away from the longitudinal axis to form the uncompressed configuration.*

*41. The implant assembly of claim 38 wherein the stopping surface is at the anterior end of the bore and defines a first opening in the attachment component.*

*42. The implant assembly of claim 38 wherein the stopping surface is perpendicular to a longitudinal axis of the bore.*

*43. A method of attaching an orthopedic implant assembly to a bone of a patient, comprising*

*a) providing an attachment member comprising*

*an attachment component which has at least one bore configured to receive a securing element with an enlarged head, the bore having a first bore portion, and a second bore portion having at least one smaller transverse dimension than transverse dimensions of the first bore portion,*

*a stopping surface which reduces a transverse configuration of the first bore portion to retain the enlarged head of a securing element within the bore of the attachment member between the stopping surface and the second bore portion;*

*b) positioning the attachment member against a surface of the patient's bone;*

*c) providing a securing element having an elongated body and an enlarged head at one end of the body which has a reversibly compressed configuration with transverse dimensions less than the reduced transverse configuration of the first bore portion formed by the stopping surface and which has an uncompressed configuration with a transverse dimension greater than the reduced transverse configuration of the second bore portion, so that the head of the securing element is retained within the second bore portion in the attachment component; and*

*d) attaching the securing element to the patient's bone by advancing the securing element within the bore of the attachment component until the enlarged head of the securing element is in the second bore portion.*

*44. An orthopedic implant assembly, comprising:*

*a. a stabilizing element having an anterior surface, a posterior surface, and at least one bore extending through the stabilizing element from the anterior surface to the posterior surface and the bore having an anterior bore portion with a transverse dimension and a posterior bore portion which has a posterior opening with a transverse dimension smaller than the transverse dimension of the anterior bore portion;*

*b. a securing element which is configured to be slidably disposed within the bore of the stabilizing element and which has an elongated body and an enlarged integral portion with a maximum transverse dimension; and*

*c. a stopping member which is at least partially disposed within the bore of the stabilizing element, which has a posterior stopping surface, a first configuration within the bore allowing passage of the securing element into the posterior bore portion with the enlarged integral portion of the securing element disposed in the posterior bore portion posterior to the stopping member and a second configuration within the bore which has smaller transverse dimensions than the first configuration and smaller than the maximum transverse dimension of the enlarged integral portion of the securing element to facilitate retention of the enlarged integral portion of the securing element within the posterior bore portion of the stabilizing element; and wherein the enlarged integral portion of the securing element is retained below the posterior surface of the stopping member.*

*45. The assembly of claim 44 wherein the stopping member is configured to prevent the back-out of the securing element through the bore of the stabilizing element.*

*46. The assembly of claim 44 wherein the stopping member is biased to the second configuration.*

*47. The assembly of claim 46 wherein the stopping member comprises a biased collar having a passageway therethrough.*

*48. The assembly of claim 47 wherein the bore has a groove in an anterior portion thereof configured to receive the biased collar, and wherein the biased collar is configured to be reversibly expandable when seated in the groove.*

*49. The assembly of claim 48 wherein the curved posterior surface of the enlarged integral portion of the securing element is configured to expand the collar as the enlarged integral portion of the securing element is displaced posteriorly through the collar passageway.*

*50. The assembly of claim 49 wherein the curved posterior surface of the enlarged integral portion of the securing element has a minimum transverse dimension smaller than a transverse dimension of the passageway of the unexpanded collar, and which is configured to contact an anterior surface of the collar and deflect the collar away from a longitudinal axis of the collar passageway as the enlarged integral portion of the securing element is displaced posteriorly through the collar passageway.*

*51. The assembly of claim 50 wherein the collar has an anterior surface which tapers toward the collar passageway.*

*52. The assembly of claim 51 wherein the posterior bore portion has a curved posterior surface that is configured to receive at least in part the curved posterior surface of the enlarged integral portion of the securing element.*

*53. The assembly of claim 44 wherein the enlarged integral portion of the securing element has a curved posterior surface.*

*54. The assembly of claim 44 wherein the enlarged integral portion of the securing element is configured to be longitudinally displaceable within the posterior bore portion of the bore of the stabilizing element.*

*55. An orthopedic implant assembly, comprising:*

*a. a stabilizing element having an anterior surface, a posterior surface, and at least one bore, the bore having an anterior bore portion, a posterior bore portion with a transverse dimension smaller than a transverse dimension of the anterior portion,*

*b. a stopping member at the anterior portion of the bore; and*

*c. a securing element having an elongated body and a head secured to the body which is reversibly compressible with a compressed transverse dimension less than the transverse dimension of the anterior portion of the bore and with an uncompressed transverse dimension greater than an inner transverse dimension of the stopping member and the posterior portion of the bore, so that the head of the securing element is retained between the stopping member and the smaller transverse dimension of the posterior portion of the bore of the stabilizing element.*

*56. The implant assembly of claim 55 wherein the head of the securing element is configured to be displaceable posteriorly through the stopping member from an anterior to a posterior surface thereof.*

*57. The implant assembly of claim 55 wherein the head of the securing element has a plurality of slots and circumferentially disposed members, the circumferentially disposed members having posterior ends secured to the body of the securing element, and anterior ends radially moveable toward a longitudinal axis of the head of the securing element to form the compressed configuration and away from the longitudinal axis to form the uncompressed configuration.*

*58. The assembly of claim 55 wherein the stopping member has a posterior surface perpendicular to a longitudinal axis of the bore.*

*59. An orthopedic attachment assembly, comprising:*

*a. an elongated securing element having an enlarged integral portion with a length, an anterior surface, a posterior surface and a transverse dimension;*

*b. an attachment element which has an anterior surface and a posterior surface and which has at least one bore extending through the attachment element from the anterior surface to the posterior surface and is configured to receive the securing element, the bore having an anterior bore portion, and a posterior bore portion, the posterior bore portion having at least one transverse dimension smaller than the transverse dimension of the enlarged integral portion of the securing element to facilitate retention of the enlarged integral portion of the securing member within the posterior bore portion; and*

*c. a biased stopping member which has a posterior stopping surface, a first configuration which extends within the bore that is elastically deformed to a second configuration as the enlarged portion of the securing member passes into the posterior bore portion, the biased stopping member returning to the first configuration upon passage of the enlarged integral portion into the posterior bore portion, the posterior stopping surface of the biased stopping member configured to engage with the anterior surface of the enlarged integral portion of the securing member facilitating retention of the enlarged portion of the securing member within the posterior bore portion of the attachment member.*

*60. The attachment assembly of claim 59 wherein*

*the first configuration of the stopping member has inner transverse dimensions that are smaller than transverse dimensions of the enlarged integral portion of the securing member to facilitate retention of the enlarged integral portion of the securing member within the posterior bore portion and*

*the second configuration of the stopping member has inner transverse dimensions that are greater than transverse dimensions of the enlarged integral portion of the securing member to allow passage of the enlarged integral portion of the securing member into the posterior bore portion.*

*61. The attachment assembly of claim 59 wherein the securing element having an enlarged integral portion is slidably disposed within the bore.*

*62. The attachment assembly of claim 61 wherein a portion of the securing member posterior to the enlarged integral portion has transverse dimensions sufficiently smaller than the transverse dimensions of the posterior bore portion so the securing member may be angularly displaced within the bore.*

*63. The attachment assembly of claim 62 wherein the posterior surface of the enlarged integral portion of the securing member is configured at least in part to conform to the posterior surface of the posterior bore portion to facilitate angulation of the securing member within the posterior bore portion.*

*64. The attachment assembly of claim 63 wherein the posterior surface of the posterior bore portion has a bowl shape.*

*65. The attachment assembly of claim 64 wherein the bowl-shaped posterior surface of the posterior bore portion at least in part is a hemispherical zone.*

*66. The attachment assembly of claim 61 wherein the securing member is selected from the group consisting of screws and nails.*

*67. The attachment assembly of claim 61 wherein a posterior surface of the posterior bore portion is configured to conform at least in part to the posterior surface of the enlarged integral portion of the securing member so as to facilitate angular displacement within the posterior bore portion.*

*68. The attachment assembly of claim 71 wherein the collar is formed of an elastically deformable material.*

*69. The attachment assembly of claim 71 wherein the collar is formed of a material selected from the group consisting of titanium and superelastic material.*

*70. The attachment assembly of claim 71 wherein the collar has a posterior surface perpendicular to a longitudinal axis of the bore extending through the attachment member.*

*71. The attachment assembly of claim 59 wherein the biased stopping member is a collar having at least in part a passageway enlargeable from a first inner dimension to a second inner dimension by the passage of the enlarged integral portion of the securing member therethrough.*

*72. The attachment assembly of claim 71 wherein the bore has a groove which receives the collar.*

*73. The attachment assembly of claim 71 wherein the enlarged integral portion of the securing member has a curved posterior surface which is configured to contact an anterior surface of the collar and expand the collar as the enlarged integral portion of the securing member is displaced posteriorly through the collar passageway.*

*74. The attachment assembly of claim 73 wherein the anterior surface of the collar tapers inwardly toward the collar passageway.*

*75. The attachment assembly of claim 59 wherein the attachment member includes at least two bores.*

*76. The attachment assembly of claim 59 wherein the attachment member is configured to conform to and extend between at least two bone segments.*

*77. The attachment assembly of claim 59 wherein the posterior surface of the attachment member is at least in part a concave surface.*

*78. The attachment assembly of claim 59 wherein the attachment member is selected from the group consisting of rods and plates.*

*79. The attachment assembly of claim 59, wherein*

*a. the enlarged integral portion of the elongated securing member has a curved posterior surface; and*

*b. the posterior bore portion has a curved posterior surface configured to conform at least in part to part of the curved posterior surface of the enlarged integral portion of the securing member received by the bore.*

*80. The assembly of claim 59 wherein the stopping element comprises a biased collar.*

*81. The assembly of claim 80 wherein the biased collar is elastically deformable to the second configuration.*

*82. The assembly of claim 81 wherein the biased collar extends at least partially within the bore of the stabilizing element.*

*83. The attachment assembly of claim 59, wherein the stopping member is a biased stopping member which reduces a transverse configuration of the anterior bore portion to retain the enlarged integral portion of the securing member within the posterior bore portion of the attachment member.*

*84. The attachment assembly of clam 59 wherein the biased stopping member resiliently returns to the first configuration after passage of the enlarged integral portion of the securing member.*

*85. The orthopedic attachment assembly of claim 59 wherein the posterior bore portion has a length sufficiently greater than the length of the enlarged integral portion of the securing element so that the enlarged integral portion of the securing element is longitudinally displaceable within the posterior bore portion when retained therein.*

*86. The orthopedic attachment assembly of claim 59 wherein,*

*a. the elongated securing element has an enlarged integral portion with a length, a posterior surface and a transverse dimension and a shaft extending from the enlarged integral portion configured to be secured within bone;*

*b. the attachment element has an anterior surface and a posterior surface and has at least one bore extending through the attachment element from the anterior surface to the posterior surface and is configured to receive the securing element, the bore having an anterior bore portion, a posterior bore portion having at least one transverse dimension smaller than the transverse dimension of the enlarged integral portion of the securing element to retain the enlarged integral portion of the securing element within the posterior bore portion; and*

*c. the stopping member defines in part a passageway in the posterior bore portion, said posterior bore portion being longer than the length of the enlarged integral portion of the securing element to allow longitudinal displacement of the enlarged integral portion of the securing element within the posterior bore portion.*

*87. The orthopedic attachment assembly of claim 86 wherein the securing element has a portion posterior to the enlarged integral portion that has a transverse dimension smaller than a transverse dimension of an opening in the posterior bore portion to provide angular displacement of the securing element within the posterior bore portion.*

*88. The orthopedic attachment assembly of claim 87 wherein the enlarged integral portion of the securing element has a maximum transverse dimension which is greater than the second transverse dimension of the stopping member.*

*89. The orthopedic attachment assembly of claim 88 wherein the enlarged integral portion of the securing element has a tapered posterior surface configured to expand the stopping member upon the passage therethrough.*

*90. The orthopedic attachment assembly of claim 86 wherein the second configuration of the stopping member has a transverse dimension that is larger than the transverse dimension of the stopping member in the first configuration.*

*91. The assembly of claim 59 wherein the posterior stopping surface of the stopping member is perpendicular to the longitudinal axis of the bore.*

*92. An orthopedic attachment assembly, comprising:*

*a. an elongated securing member having a biased enlarged portion with a length, an anterior surface, a posterior surface and a transverse dimension;*

*b. an attachment member which has an anterior surface and a posterior surface and which has at least one bore extending through the attachment member from the anterior surface to the posterior surface and is configured to receive the securing member, the bore having an anterior bore portion, a posterior bore portion having at least one transverse dimension smaller than the transverse dimension of the biased enlarged portion of the securing member to facilitate retention of the enlarged portion of the securing member within the posterior bore portion; and*

*c. a stopping member which has an anterior surface, and a posterior stopping surface which extends within the bore;*

*d. the biased enlarged portion of the securing member is elastically deformed from a first configuration to a second configuration as the biased enlarged portion passes the stopping member during the passage of the biased enlarged portion of the securing member into the posterior bore portion of the attachment member, the biased enlarged portion of the securing member returning to the first configuration after passage of the biased enlarged portion into the posterior bore portion of the attachment member, engagement of the posterior stopping surface of the stopping member with the anterior surface of the biased enlarged portion of the securing member facilitating retention of the biased enlarged integral portion of the securing member within the posterior bore portion of the attachment member.*

*93. The orthopedic implant assembly of claim 92 wherein the biased enlarged portion of the securing element comprises at least one resilient member that deflects longitudinally when the securing element is advanced posteriorly through the bore of the stabilizing element.*

*94. The assembly of claim 92 wherein the biased enlarged portion of the securing element comprises a biased collar.*

*95. The assembly of claim 92 wherein the compressible part of the enlarged portion of the securing element comprises at least one circumferentially disposed member.*

*96. The assembly of claim 95 wherein the at least one circumferentially disposed member has a posterior end secured to the shaft of the securing element.*

*97. The assembly of claim 96 wherein the securing element comprises a plurality of circumferentially disposed members having posterior ends secured to the shaft of the securing element.*

*98. An orthopedic attachment assembly, comprising:*

*a. an elongated securing element having an enlarged integral portion with a length, an anterior surface, a posterior surface and a transverse dimension;*

*b. an attachment member which has an anterior surface and a posterior surface and which has at least one bore extending through the attachment member from the anterior surface to the posterior surface and is configured to receive the securing element, the bore having an anterior bore portion, a posterior bore portion having at least one transverse dimension smaller than the transverse dimension of the enlarged integral portion of the securing element; and*

*c. a plurality of biased stopping members that are part of the attachment member, each of said stopping members having a posterior stopping surface, a first configuration wherein the stopping members extend within the bore and wherein the stopping members are elastically deformed by the passage of the enlarged portion of the securing element to a second configuration to allow passage of the enlarged portion of the securing element into the posterior bore portion, the biased stopping members returning to the first configuration upon passage of the enlarged portion and the posterior stopping surfaces configured to engage the anterior surface of the securing element facilitating retention of the enlarged integral portion of the securing element within the posterior bore portion of the attachment member.*

*99. The orthopedic implant assembly of claim 98 wherein the biased stopping members are contractible fingers.*

*100. The orthopedic implant assembly of claim 98 wherein the plurality of biased stopping members comprise resilient longitudinally deflectable members which have first un-deflected configurations within the anterior bore portion and deflected configurations which allow the enlarged integral portion of the securing element to pass into the posterior bore portion, the one or more deflectable members having posterior surfaces that are configured to engage an anterior surface of the enlarged integral portion of the securing element to prevent the back-out of the enlarged integral head of the securing element from the posterior bore of the stabilizing element and facilitate retention of the enlarged integral head of securing element within the posterior bore portion.*

*101. An orthopedic implant assembly, comprising:*

*a. a stabilizing element having an anterior surface, a posterior surface, and at least one bore extending through the stabilizing element from the anterior surface to the posterior surface with an anterior bore portion which has a transverse dimension, a posterior bore portion which has a posterior opening with a transverse dimension smaller than the transverse dimension of the anterior bore portion;*

*b. a securing element having an elongated body and an enlarged integral portion having an anterior surface; and*

*c. a biased stopping member which has a posterior stopping surface, which has a first configuration within the anterior bore portion that has a first transverse dimension and is elastically deformable to a second configuration within the anterior bore portion that has a second transverse dimension larger than the first transverse dimension that allows the enlarged integral portion of the securing element to pass into the posterior bore portion posterior to the biased stopping member, the biased stopping member returning to the first configuration so that the posterior surface of the stopping member is positioned to engage the anterior surface of the securing element and prevents the securing element from backing out of the posterior bore portion and to facilitate retention of the enlarged integral portion of the securing element within the posterior bore portion.*

*102. The orthopedic implant assembly of claim 101 wherein the biased stopping member elastically returns from the first configuration back to the second configuration.*

*103. The assembly of claim 101 wherein the biased stopping member comprises a collar.*

*104. The assembly of claim 103 wherein the biased collar is disposed in part within a recess of the stabilizing element.*

*105. The assembly of claim 104 wherein the recess is a groove configured to slidably receive the biased collar.*

* * * * *

UNITED STATES PATENT AND TRADEMARK OFFICE

CERTIFICATE OF CORRECTION

PATENT NO. : RE43,008 E
APPLICATION NO. : 10/620154
DATED : December 6, 2011
INVENTOR(S) : David J. Talaber and James R. Lloyd It is certified that error appears in the above-identified patent and that said Letters Patent is hereby corrected as shown below:

On the title page, item (73) assignee

Change: "Assignee: Acantha, Inc." to --Assignee: ACANTHA LLC--.

Signed and Sealed this
Thirty-first Day of March, 2015

Michelle K. Lee

Michelle K. Lee
*Director of the United States Patent and Trademark Office*